United States Patent
Leipertz (10) Patent No.: US 7,084,963 B2
(45) Date of Patent: Aug. 1, 2006

(54) METHOD AND DEVICE FOR THE COMPREHENSIVE CHARACTERIZATION AND MONITORING OF EXHAUST GASES AND THE REGULATION OF ENGINES IN PARTICULAR INTERNAL COMBUSTION ENGINES AND COMPONENTS FOR THE TREATMENT OF EXHAUST GAS

(75) Inventor: Alfred Leipertz, Erlangen (DE)

(73) Assignee: Esytec energie- Und Systemtechnik GmbH, Erlangen (DE)

( * ) Notice: Subject to any disclaimer, the term of this patent is extended or adjusted under 35 U.S.C. 154(b) by 317 days.

(21) Appl. No.: 10/477,200
(22) PCT Filed: May 8, 2002
(86) PCT No.: PCT/EP02/05042
§ 371 (c)(1), (2), (4) Date: Nov. 17, 2003
(87) PCT Pub. No.: WO02/095376
PCT Pub. Date: Nov. 28, 2002

(65) Prior Publication Data
US 2004/0237505 A1 Dec. 2, 2004

(30) Foreign Application Priority Data
May 18, 2001 (DE) .............................. 101 24 235

(51) Int. Cl.
G01N 21/65 (2006.01)
G01N 21/64 (2006.01)
G01N 21/63 (2006.01)
(52) U.S. Cl. ................... 356/73; 356/301; 356/318; 250/339.13; 250/343
(58) Field of Classification Search ............ 356/72, 356/73, 301, 317, 318; 250/339.03, 339.13, 250/343
See application file for complete search history.

(56) References Cited

U.S. PATENT DOCUMENTS 3,625,613 A * 12/1971 Abell et al. ............... 356/301

(Continued)

FOREIGN PATENT DOCUMENTS

DE 4235225 6/1994

(Continued)

OTHER PUBLICATIONS

A. Ciucci et al., Appl. Phys. B 63 (1996) pp. 185-190.

(Continued)

*Primary Examiner*—F. L. Evans
(74) *Attorney, Agent, or Firm*—Greenblum & Bernstein, P.L.C.

(57) ABSTRACT

Device of modular construction which permits the simultaneous or not-simultaneous recording and characterization of solid and liquid particles and gaseous components of engine exhaust gases on various test supports, with only small or no modification of the test support. Methods are based on individual or combined usage of laser scattering techniques, laser-induced breakdown spectroscopy, laser-induced ionization spectroscopy, laser-induced atomic fluorescence spectroscopy, IR-/VIS-/UV-laser absorption spectroscopy and laser-induced incandescence. Use of individual or combined usage of such devices permits the analysis of raw exhaust gas, the conditioned and/or treated exhaust gases for monitoring and checking working pattern of engine, individual components of exhaust gas treatment and/or total system on test beds and on vehicle and can be used for control of motor and/or exhaust components, such as catalysts and particle filters, on test beds and in driven usage, e.g., in connection with, or as part of, on-board diagnostic system.

66 Claims, 4 Drawing Sheets

U.S. PATENT DOCUMENTS

| | | | |
|---|---|---|---|
| 4,990,780 A | * | 2/1991 | Lee et al. ............... 250/343 |
| 5,241,367 A | | 8/1993 | Grob et al. |
| 5,252,828 A | * | 10/1993 | Kert et al. ............ 250/339.13 |
| 5,490,490 A | * | 2/1996 | Weber et al. ............ 123/697 |
| 5,709,082 A | * | 1/1998 | Harris et al. ............ 60/276 |
| 5,777,748 A | * | 7/1998 | Stengel ................. 356/438 |

FOREIGN PATENT DOCUMENTS

| | | |
|---|---|---|
| DE | 19006005 | 4/1997 |
| DE | 19541516 | 5/1997 |
| DE | 19702006 | 7/1998 |
| DE | 19827533 | 12/1999 |
| DE | 19904691 | 9/2000 |
| DE | 19944006 | 3/2001 |

OTHER PUBLICATIONS

.D.K. Ottesen, Proc. 24$^{th}$ Combustion Symposium, 1992, p. 1579-1585.

A. Weber (ed.), *Raman Spectroscopy of Gases and Liquids*, Springer-Verlag, Berlin 1979.

H.W. Schrötter and H.W. Klöckner, *Raman scattering cross sections in gases and liquids*, p. 123-166.

A. Leipertz, Dissertation, Ruhr University Bochum, 1979, pp. 48-51, and 144-161.

A. Leipertz, Habilitationsschrift, Ruhr Universität Bochum 1984 (p. 380-382).

Hirschberger R., *Simultane Online-Analyse Von Abgasen Mit Einen Laser-Raman-Polychromator*, Mtz Motortechnische Zeitschrift, Franckh'Sche Verlagshandlung, Abteilung Technik. Stuttgart, DE, vol. 57, No. 3, Mar. 1, 1996 pp. 184-191, XP000558297, ISSN: 0024-8525.

Arca G et al., *Detection of Environmental Contaminants by Time Resolved Laser Induced Breakdown Spectroscopy Technique*, Igarss 1996. International Geoscience and Remote Sensing Symposium. Remote Sensing for a Sustainable Future, Lincoln, NE, May 28-31, 1996, International Geoscience and Remote Sensing Symposium, Igarss, New York, IEEE, US, vol. 2, May 28, 1996, pp. 854-856, XP000633738, ISBN: 0-7803-3069-2.

Buckley S.G. et al., *Implementation of Laser-Induced Breakdown Spectroscopy as a Continuous Emissions Monitor for Toxic* Waste Management, Elsevier, New York, NY, US, vol. 20, No. 5-6, Oct. 2000, pp. 455-462, XP004204551, ISSN: 0956-053X.

Snelling et al., SAE Paper 1999-01-3653, (1999) pp. 1-9, XP001068150.

* cited by examiner

METHOD AND DEVICE FOR THE COMPREHENSIVE CHARACTERIZATION AND MONITORING OF EXHAUST GASES AND THE REGULATION OF ENGINES IN PARTICULAR INTERNAL COMBUSTION ENGINES AND COMPONENTS FOR THE TREATMENT OF EXHAUST GAS

CROSS-REFERENCE TO RELATED APPLICATIONS

The present application is a National Stage Application of International Application No. PCT/EP02/05042, filed May 8, 2002. Further, the present application claims priority under 35 U.S.C. § 119 of German Patent Application No. 101 24 235.2 filed on May 18, 2001.

BACKGROUND OF THE INVENTION

Field of the Invention

To comply with future regulations on exhaust gases, measuring, monitoring and regulating systems will be required which can record the preset exhaust gas values and monitor compliance with them as well as, if possible, regulate the combustion system and/or frequently downstream positioned components of the exhaust gas aftertreatment, e.g., catalytic converter systems or filter systems, with these measured or control values towards the desired emissions or provide the corresponding regulating variables in the control system. Such systems that, if possible, comprehensively characterize the exhaust gas, i.e., that record all the gaseous, liquid and solid constituents as far as possible at the same time, will be increasingly used in future in the research laboratories and test beds of the auto industry and its suppliers, in the service centers (e.g., comparable with today's Bosch test centers) and, at least in partial areas, also in the motor vehicle itself, e.g., as part of an on-board diagnostics (OBD) system. In addition to the monitoring, improvement and regulation of the internal combustion engine via measurements in the raw exhaust gas, these systems can likewise also be used for stand-alone or integrated components for exhaust gas aftertreatment through measurements before and/or after the respective components, e.g., the catalytic converters for treating gaseous and/or particulate exhaust gas constituents or the corresponding filter systems, thus, e.g., also for monitoring and regulating the regeneration process of particle filters.

SUMMARY OF THE INVENTION

The subject matter of the invention is the individual, specific—but in particular also the joint-use of different optical, mostly laser-based, laser diode-based or diode laser-based measuring processes for characterizing exhaust gas and individual components important for characterizing exhaust gas and the combination of devices that combine these measuring processes in a targeted manner. Some of the methods are already known or have already been tested for the individual task, but have not been used simultaneously with other methods in this combination. Other methods have not yet been used even individually in the field of application targeted here and thus also represent an independent invention in their individual use.

Engine exhaust gases comprise gaseous constituents (e.g., oxygen, unburned fuel constituents such as hydrocarbons or hydrogen itself, carbon monoxide and carbon dioxide, nitrogen monoxide, nitrogen dioxide and $N_2O$, sulfur compounds, etc.) and particulates that can be present in liquid form (e.g., as condensates, such as water, sulfuric acid, etc., or aqueous solutions, e.g., urea-water solutions in connection with catalytic converter systems) or in solid form (e.g., soot particles, metal compounds, ash, etc.) often also with organic deposits or, e.g., also deposits of sulfur compounds thereon. In this invention different measuring methods and processes are listed and used in part in combination and simultaneously for recording and characterizing these different constituents.

Solid particles of the exhaust gas include soot particles (pure carbon) that with the aid of the laser-induced incandescence process (also called laser-induced incandescence (LII)) can be comprehensively (German Patent DE 19606005) and simultaneously (German Patent Application DE 19904691 A1) characterized with regard to its volume or mass concentration, its primary particle size, its aggregate size and values that can be derived therefrom. This process is used here according to the invention for the first time in combination with individual or several other measuring processes referenced in this invention. The laser (or diode laser) used here to excite the thermal particle radiation or the laser diode used to this end is also used simultaneously or one after the other as an excitation light source for individual or several of the other measuring processes. Alternatively, one or more other excitation beam sources can be used parallel thereto with the same beam course in the measurement volume or spatially displaced thereto in one or more other beam courses in the measurement volume. The detection of the LII signal can take place offset in time to the measurement signals of individual or of all other processes with in part the same detection beam course in that conditional on the process for the other measuring processes in partial branches of the registration beam course other optical components can be combined or can take place simultaneously using different detection beam courses, whereby all of these detection beam courses or individual beam courses can be executed in the backscattering direction relative to the input beam direction; however they can also have any other direction arranged at an angle to the input beam direction, whereby conditional on the system an arrangement at 90 degrees or 180 degrees is advantageous in some processes. Records of the measurement signals of the different processes in selected, in part also different, spectral regions takes place via wavelength-selective optical components, e.g., filters, spectrometers, monochromators, etc., with photomultipliers, photodiodes, streak cameras, CCD cameras or similar optoelectronic components that can produce electrical signals from optical measurement signals. These electrical signals can be further processed for imaging the measurement signals, for data processing and/or also used directly for regulating purposes. Three possible arrangements for three different measuring processes for a mainly backscattering arrangement (FIG. 1), a 90-degree arrangement (FIG. 2) and a 180-degree arrangement (FIG. 3) are shown diagrammatically according to the device by way of example in FIGS. 1 through 3. The pipe segments described in patent application DE 19904691 A1 can be used advantageously in particular for measurements in exhaust gas, which pipe segments there integrate all the features essential for the LII sensor and in this invention at the same time also integrate the essential features of the other processes.

The other measuring processes to be used respectively alone or also in combination with the LII technique or with one another at the same time or one after the other characterize other components of the engine exhaust gas.

Solid constituents of the exhaust gas are furthermore particles of different metals, partially in almost pure form, as metal oxides or as metal compounds of another kind, silicon compounds and ash. A characterization, e.g., identification and concentration of the individual constituents, is possible, e.g., via laser-induced ionization spectroscopy (LIS)—often called laser-induced breakdown spectroscopy (LIBS) in specialized scientific literature in a special embodiment using highly tempered plasmas and also thus termed below in this patent specification—in which via the laser action, parts of the particles or the particle as a whole is vaporized and partially ionized. Specifically this occurs with LIBS in that during the irradiation of an extremely high power density of over a hundred MW/cm$^2$ a high-temperature microplasma of high electron density is produced with temperatures of several thousand degrees, at which every material is decomposed, evaporated and ionized. The subsequent radiation is at first wide-band (from the x-ray region to infrared), after a brief time lag—with cooled down plasma with neutral atoms in excited states—species-selective regarding the atoms present (e.g., for Al, Ba, Ca, Co, Cr, Cu, Eu, Fe, Hg, Mg, Mn, Mo, Na, Ni, Pb, Sb, Si, Sr, Ti, V, W and Zn in A. Ciucci et al., Appl. Phys. B 63 (1996) 185–190) and can be assigned to different atomic constituents, e.g., via comparisons with spectra known from the literature and/or via calibrated measurements or laboratory measurements. In this manner ashes or such deposits (D. K. Ottesen, Proc. 24$^{th}$ Combustion Symposium, 1992, p. 1579–1585) or deposits on the solid particles can also be identified and measured. Laser-induced breakdown spectroscopy (LIBS) is used here according to the invention for the first time to test the exhaust gas of engine combustion processes or the exhaust gas treated by way of catalytic converters or filters, which can be implemented alone or also in combination with other processes. This technique thus represents by way of example in simultaneous use with LII one of the processes in FIGS. 1 through 3.

The soot particles as solid particles can likewise be detected and measured by way of the LIBS technique, either simultaneously with other solid particles or alone. This technique can likewise be used for characterizing liquid particles and gaseous constituents.

If the solid, liquid or gaseous constituents to be detected are present in amounts that are below the LIBS detection limit (approx. 100 ppb), as an alternative to LIBS, laser atomic fluorescence spectroscopy (LAFS) is used, for example, which is thus accordingly used according to the invention for such low detection limits in engine exhaust gases.

Liquid constituents of the raw exhaust gas behind the engine and/or of the treated exhaust gas after components of the exhaust gas aftertreatment can comprise, e.g., water, sulfuric acid, nitric acid or urea-water solutions or can be contained therein. To test and characterize such exhaust gas constituents according to the invention here for the first time the laser Raman scattering (LRS) technique is used in linear (spontaneous) or also in non-linear form, alone or in combination with LII and/or one or more of the other processes. It is excited via lasers (also diode lasers) or laser diodes, to which end an excitation light source specifically for this process or the excitation light source of the LII technology or that of another process can be used, whereby in a process-specific favorable manner the shortest possible excitation wavelengths are selected that can also be realized, e.g., through a frequency multiplication of the output radiation of a laser likewise used for another process. The Raman scattered light spectrally shifted due to the light-molecule interaction in a molecule-specific manner according to the Raman shift (G. Herzberg, *Molecular Spectra and Molecular Structure*, vol. I through III, Krieger Publ. Company, Malabar, Fla., 1989 or 1991; vol. IV with G. Huber, Van Nostrand, Princeton-New York, 1979; P. W. B. Pearse and A. G. Gaydon, *The Identification of Molecular Spectra*, Chapman and Hall, London 1976; B. Schrader, ed., *Infrared and Raman Spectroscopy*, VCH Verlagsgesellschaft, Weinheim 1995) after spectral selection by way of, e.g., interference filters or spectrometers or monochromators is conveyed to detectors of the above-mentioned type, whereby it has a favorable effect that the relatively small scattering cross section for gases is considerably larger for liquids (A. Weber (ed.), *Raman Spectroscopy of Gases and Liquids*, Springer-Verlag, Berlin 1979, and therein specifically H. W. Schrötter and H. W. Klöckner, *Raman scattering cross sections in gases and liquids*, p. 123–166) and this technique can thus be used according to the invention. This can take place individually or in combination with other techniques with, e.g., one of the devices shown diagrammatically in FIGS. 1 through 3, in particular favorably in a right-angled arrangement (FIG. 2) between input beam direction and detection direction. Evaluating the spectra and obtaining results takes place in fundamentally the same ways as is given for gas phase Raman spectroscopy and described, e.g., in A. Leipertz, Dissertation, Ruhr University Bochum, 1979; A. Leipertz, Habilitationsschrift, Ruhr Universität Bochum 1984 (p. 380–382 regarding a concentration measurement), in invention DE 19827533 for determining the vapor phase composition in evaporating injection sprays or in patent application DE 19702006 A1 for determining calorific value by way of Raman scattering. Water can thus be measured with relatively wide vibration bands, e.g., with Raman shifts of approx. 675, approx 1640 and approx. 3400 wave numbers, sulfuric acid, i.a., via the $SO_4^{2-}$ vibration at approx. 980 wave numbers and nitric acid, e.g., at 1045 wave numbers. For these constituents and others of interest there is a plurality of other Raman shifts that can be used likewise and/or alternatively, which increase in number with increasing complexity of the molecule according to the increasing number of possible vibration states and which can be taken from many publications on Raman spectroscopy and, e.g., from the above-mentioned books and publications.

Since material in solid aggregate form, and thus also the solid particles of engine exhaust gas, is also Ramon-active, alternatively to LIBS, LRS—or non-linear forms of Raman scattering—are also used according to the invention to investigate the solid particles.

For the gaseous exhaust gas constituents $NO_x$, NO, $NO_2$, $N_2O$, CO, HC limited by international agreements or draft agreements as well as, e.g., $H_2O$ and $NH_3$, there are measuring systems commercially available (e.g., on the basis of the chemical luminescence technique, infrared absorption spectroscopy, preferably in the near infrared region, e.g., also as Fourier Transform Infrared (FTIR) analyzers, as flame ionization detectors, etc.). However, so far none of them have been used directly in the exhaust gas pipe—so in principle only via specimen-taking procedures—or in combination with particle detection systems, as is here introduced for the first time according to the invention. In addition to the liquid phase, according to the invention here the same constituents in gas or vapor form are also recorded and measured via the Raman scattering with the same or different Raman shift (water, e.g., with a Raman shift of approx. 1595 or approx. 3652 wave) numbers or additionally also e.g., $NH_3$ (e.g., with a Raman shift of approx. 3334 wave numbers), $SO_2$ (e.g., with a Raman shift of approx. 519 and approx. 1151 wave numbers), etc., and in particular the components occurring with high concentrations. Alternatively, or also additionally in this invention the determination and measurement of these gaseous constituents are carried out advantageously with variable lasers, laser diodes or diode lasers which via absorption spectroscopy in the infrared, visible and/or ultraviolet spectral region make it possible to test several constituents with only one absorption light source, or with different absorption light sources (laser (diode) absorption technique—LAT) selected for the respective constituents. In addition, oxygen is also measured, in order to thus conduct, e.g., an engine control according to today's 8 probes with a 8 probe working across the entire concentration range, e.g., according to invention DE 19541516. Independent of a device according to FIGS. 1–3, or also in combination with one like this, a transmitted light arrangement for stretching the necessary absorption lengths is used in the absorption techniques, whereby to extend the absorption length a multi-pass arrangement e.g., made of reflecting mirrors, is selected sweeping over the measurement volume, or also one such outside the exhaust gas main stream (e.g., in a bypass arrangement) where alternatively simple measurement cells of corresponding length are also used.

The invention also provides for a process for determining properties of liquid particles of engine exhaust gas, wherein the process comprises detecting Raman scattering produced in a test area by excitation with one of a laser, a laser diode, and a diode laser and determining at least one of a type and composition of individual constituents of the liquid particles of the engine exhaust gas and concentrations of individual constituents of the liquid particles of the engine exhaust gas.

The determining may comprise determining concentrations of the individual constituents of the liquid particles of the engine exhaust gas, and wherein the concentrations of individual constituents of the liquid particles of the engine exhaust gas comprise at least one of a number concentration, a mass concentration, and a volume concentration.

The determining may comprise determining concentrations, via partial densities, of the individual constituents of the liquid particles of the engine exhaust gas, and wherein the concentrations of individual constituents of the liquid particles of the engine exhaust gas comprise at least one of a number concentration, a mass concentration, and a volume concentration.

The engine exhaust gas may be in a raw state. The engine exhaust gas may be at least one of conditioned exhaust gas and diluted exhaust gas. The engine exhaust gas may comprise one of water, sulfuric acid, nitric acid, water in pure form, sulfuric acid in pure form, nitric acid in pure form. The engine exhaust gas may comprise at least one of other constituents and aqueous solutions. The engine exhaust gas may comprise an urea water solution. The engine exhaust gas may comprise a mixture of one of water, sulfuric acid, nitric acid, and water in pure form, sulfuric acid in pure form, nitric acid in pure form. The process may determine properties of liquid particles of engine exhaust gas behind components of exhaust gas aftertreatment.

The invention also provides for a process for determining properties of solid particles of engine exhaust gas, wherein the process comprises detecting Raman scattering produced in a test area by excitation with one of a laser, a laser diode, and a diode laser and determining at least one of a type and composition of individual constituents of the solid particles of the engine exhaust gas and concentrations of individual constituents of the solid particles of the engine exhaust gas.

The determining may comprise determining concentrations of individual constituents of the solid particles of the engine exhaust gas, and wherein the concentrations of individual constituents of the solid particles of the engine exhaust gas comprise at least one of a number concentration, a mass concentration, and a volume concentration.

The determining may comprise determining concentrations of individual constituents of the solid particles of the engine exhaust gas, and wherein the concentrations of individual constituents of the solid particles of the engine exhaust gas comprise at least one of a number concentration, a mass concentration, and a volume concentration.

The engine exhaust gas may be in a raw state. The engine exhaust gas may be at least one of conditioned exhaust gas and diluted exhaust gas. The solid particles may comprise one of soot particles, metals, metal oxides, metal compounds, silicon compounds, and ash. The process may determine properties of solid particles of engine exhaust gas behind components of exhaust gas aftertreatment.

The invention also provides for a process for determining a concentration of gaseous constituents of engine exhaust gas, wherein the process comprises detecting Raman scattering produced in a test area by excitation with one of a laser, a laser diode, and a diode laser and determining a type and concentration of individual gaseous constituents of the engine exhaust gas.

The determining may comprise determining a type and concentration, via partial densities, of individual gaseous constituents of the engine exhaust gas. The concentration of individual gaseous constituents of engine exhaust gas may comprise one of a number concentration of individual gaseous constituents of engine exhaust gas, a mass concentration of individual gaseous constituents of engine exhaust gas, and a volume concentration of individual gaseous constituents of engine exhaust gas.

The engine exhaust gas may be in a raw state. The engine exhaust gas may be at least one of conditioned exhaust gas and diluted exhaust gas. The individual gaseous constituents may comprise $NO_x$, NO, $NO_2$, $N_2O$, CO, HC, $O_2$, $H_2O$, and $NH_3$. The process may determine a concentration of gaseous constituents of engine exhaust gas behind components of exhaust gas aftertreatment.

The invention also provides for a process for determining properties of solid particles of engine exhaust gas, wherein the process comprises detecting radiation produced in a test area by laser-induced breakdown spectroscopy (LIBS) after irradiation with one of a laser, a laser diode, and a diode laser and determining a type and composition of the solid particles of the engine exhaust gas.

The engine exhaust gas may be in a raw state. The engine exhaust gas may be at least one of conditioned exhaust gas and diluted exhaust gas. The solid particles may comprise one of soot particles, metals, metal oxides, metal compounds, silicon compounds, and ash. The process may determine properties of solid particles of engine exhaust gas behind components of exhaust gas aftertreatment.

The invention also provides for a process for determining properties of solid particles of engine exhaust gas, wherein the process comprises detecting radiation produced in a test area after irradiation with one of a laser, a laser diode, and a diode laser, and after vaporization and ionization of one of the solid particles and parts of the solid particles and determining a type and composition of the solid particles of the engine exhaust gas.

The engine exhaust gas may be in a raw state. The engine exhaust gas may be at least one of conditioned exhaust gas and diluted exhaust gas. The solid particles may comprise one of soot particles, metals, metal oxides, metal compounds, silicon compounds, and ash. The process may determine properties of solid particles of engine exhaust gas behind components of exhaust gas aftertreatment.

The invention also provides for a process for determining properties of liquid particles of engine exhaust gas, wherein the process comprises detecting radiation produced in a test area after irradiation with one of a laser, a laser diode, and a diode laser, and after vaporization and ionization of one of the liquid particles and parts of the liquid particles and determining a type and composition of the liquid particles of the engine exhaust gas.

The engine exhaust gas may be in a raw state. The engine exhaust gas may be at least one of conditioned exhaust gas and diluted exhaust gas. The engine exhaust gas may comprise one of water, sulfuric acid, nitric acid, water in pure form, sulfuric acid in pure form, nitric acid in pure form. The engine exhaust gas may comprise at least one of other constituents and aqueous solutions. The engine exhaust gas may comprise an urea water solution. The engine exhaust gas may comprise a mixture of one of water, sulfuric acid, nitric acid, and water in pure form, sulfuric acid in pure form, nitric acid in pure form. The process may determine properties of liquid particles of engine exhaust gas behind components of exhaust gas aftertreatment.

The invention also provides for a process for determining properties of liquid particles of engine exhaust gas, wherein the process comprises detecting radiation produced in a test area by laser-induced breakdown spectroscopy (LIBS) after irradiation with one of a laser, a laser diode, and a diode laser and determining a type and composition of the liquid particles of the engine exhaust gas.

The engine exhaust gas may be in a raw state. The engine exhaust gas may be at least one of conditioned exhaust gas and diluted exhaust gas. The engine exhaust gas may comprise one of water, sulfuric acid, nitric acid, water in pure form, sulfuric acid in pure form, nitric acid in pure form. The engine exhaust gas may comprise at least one of other constituents and aqueous solutions. The engine exhaust gas may comprise an urea water solution. The engine exhaust gas may comprise a mixture of one of water, sulfuric acid, nitric acid, and water in pure form, sulfuric acid in pure form, nitric acid in pure form. The process may determine properties of liquid particles of engine exhaust gas behind components of exhaust gas aftertreatment.

The invention also provides for a process for determining concentrations of gaseous constituents of engine exhaust gas, wherein the process comprises detecting radiation produced in a test area by laser-induced breakdown spectroscopy (LIBS) after irradiation with one of a laser, a laser diode, and a diode laser and determining a type and concentration of individual gaseous constituents of the engine exhaust gas.

The concentration of individual gaseous constituents of engine exhaust gas may comprise one of a number concentration of individual gaseous constituents of engine exhaust gas, a mass concentration of individual gaseous constituents of engine exhaust gas, and a volume concentration of individual gaseous constituents of engine exhaust gas.

The engine exhaust gas may be in a raw state. The engine exhaust gas may be at least one of conditioned exhaust gas and diluted exhaust gas. The individual gaseous constituents may comprise $NO_x$, $NO$, $NO_2$, $N_2O$, $CO$, $HC$, $O_2$, $H_2O$, and $NH_3$. The process may determine concentrations of gaseous constituents of engine exhaust gas behind components of exhaust gas aftertreatment.

The invention also provides for a process for determining properties of at least one of liquid particles and solid particles of engine exhaust gas, wherein the process comprises detecting an atomic fluorescence emission produced in a test area by excitation with one of a laser, a laser diode, and a diode laser and determining a type and composition of the liquid and/or solid particles of the engine exhaust gas and concentrations of individual constituents.

The engine exhaust gas may be in a raw state. The engine exhaust gas may be at least one of conditioned exhaust gas and diluted exhaust gas.

The process may further comprise determining concentrations of individual constituents, which concentrations comprise at least one of a number concentration, a mass concentration and a volume concentration.

The process may further comprise calculating concentrations of individual constituents using at least one of a measuring signal and an atomic fluorescence measuring signal.

The process may further comprise, after ionization, calculating concentrations of individual constituents using at least one of a measuring signal and an atomic fluorescence measuring signal.

The engine exhaust gas may comprise one of water, sulfuric acid, nitric acid, water in pure form, sulfuric acid in pure form, nitric acid in pure form. The engine exhaust gas may comprise at least one of other constituents and aqueous solutions. The engine exhaust gas may comprise an urea water solution. The engine exhaust gas may comprise a mixture of one of water, sulfuric acid, nitric acid, and water in pure form, sulfuric acid in pure form, nitric acid in pure form. The solid particles may comprise one of soot particles, metals, metal oxides, metal compounds, silicon compounds, and ash. The process may determine properties of at least one of liquid particles and solid particles of engine exhaust gas behind components of exhaust gas aftertreatment.

The invention also provides for a process for determining concentrations of gaseous constituents of engine exhaust gas, wherein the process comprises detecting parts of laser radiation absorbed after irradiation in a test area with one of a variable laser, a variable laser diode, and a variable diode laser and determining a type and concentration of individual gaseous constituents of the engine exhaust gas.

The detecting may comprise detecting parts of laser radiation, in at least one of an infrared spectral region, a visible spectral region, and an ultraviolet spectral region, absorbed after irradiation in a test area with one of a variable laser, a variable laser diode, and a variable diode laser.

The engine exhaust gas may be in a raw state. The engine exhaust gas may be at least one of conditioned exhaust gas and diluted exhaust gas. The concentration of individual gaseous constituents may comprise at least one of a number concentration, a mass concentration and a volume concentration. The engine exhaust gas may comprise one of water, sulfuric acid, nitric acid, water in pure form, sulfuric acid in pure form, nitric acid in pure form. The engine exhaust gas may comprise at least one of other constituents and aqueous solutions. The engine exhaust gas may comprise an urea water solution. The engine exhaust gas may comprise a mixture of one of water, sulfuric acid, nitric acid, and water in pure form, sulfuric acid in pure form, nitric acid in pure form. The individual gaseous constituents may comprise $NO_x$, $NO$, $NO_2$, $N_2O$, $CO$, $HC$, $O_2$, $H_2O$, and $NH_3$. The process may determine concentrations of gaseous constituents of engine exhaust gas behind components of exhaust gas aftertreatment.

The invention also provides for a device for practicing any of the processes described above wherein device comprises a detector unit and a plurality of optical components.

The invention also provides for a device for practicing any of the processes described above wherein device comprises a detector unit comprising one of optical fibers and parts of optical fibers.

The invention also provides for a device for practicing any of the processes described above wherein device comprises a device enclosing the engine exhaust gas and a device for one of avoiding contamination and reducing contamination.

The invention also provides for a system for determining concentrations of gaseous constituents of engine exhaust gas, wherein the system comprises a test area comprising an optical access, a light source emitting an optical beam towards the optical access, the light source comprising one of a laser, a laser diode, and a diode laser, an optical device disposed between the optical access and the light source, at least one detector unit receiving an optical beam passing through the optical device from the optical access, and an electronic processing system communicating with the at least one detector unit.

The invention also provides for a system for determining concentrations of gaseous constituents of engine exhaust gas, wherein the system comprises a test area comprising a first optical access and a second optical access, a light source emitting an optical beam towards the first optical access, the light source comprising one of a laser, a laser diode, and a diode laser, an optical device disposed between the first optical access and the light source, at least one detector unit receiving an optical beam from the second optical access, and an electronic processing system communicating with the at least one detector unit.

The invention also provides for a process for determining properties of solid particles of engine exhaust gas, wherein the process comprises detecting radiation produced in a test area by laser-induced breakdown spectroscopy (LIBS) after irradiation with one of a laser, a laser diode, and a diode laser, detecting radiation produced in the test area by laser-induced incandescence (LII) after irradiation with one of a laser, a laser diode, and a diode laser, and determining a type and composition of the solid particles of the engine exhaust gas.

The invention also provides for a process for determining properties of liquid particles of engine exhaust gas, wherein the process comprises detecting radiation produced in a test area by laser-induced breakdown spectroscopy (LIBS) after irradiation with one of a laser, a laser diode, and a diode laser, detecting radiation produced in the test area by laser-induced incandescence (LII) after irradiation with one of a laser, a laser diode, and a diode laser, and determining a type and composition of the liquid particles of the engine exhaust gas.

The invention also provides for a process for determining concentrations of gaseous constituents of engine exhaust gas, wherein the process comprises detecting radiation produced in a test area by laser-induced breakdown spectroscopy (LIBS) after irradiation with one of a laser, a laser diode, and a diode laser, detecting radiation produced in the test area by laser-induced incandescence (LII) after irradiation with one of a laser, a laser diode, and a diode laser, and determining a type and concentration of individual gaseous constituents of the engine exhaust gas.

The invention also provides for a A process for determining properties of liquid particles of engine exhaust gas, wherein the process comprises detecting Raman scattering produced in a test area by excitation with one of a laser, a laser diode, and a diode laser, detecting radiation produced in the test area by laser-induced incandescence (LII) after irradiation with one of a laser, a laser diode, and a diode laser, and determining at least one of a type and composition of individual constituents of the liquid particles of the engine exhaust gas, and concentrations of individual constituents of the liquid particles of the engine exhaust gas.

The invention also provides for a process for determining properties of solid particles of engine exhaust gas, wherein the process comprises detecting Raman scattering produced in a test area by excitation with one of a laser, a laser diode, and a diode laser, detecting radiation produced in the test area by laser-induced incandescence (LII) after irradiation with one of a laser, a laser diode, and a diode laser, and determining at least one of a type and composition of individual constituents of the solid particles of the engine exhaust gas, and concentrations of individual constituents of the solid particles of the engine exhaust gas.

BRIEF DESCRIPTION OF THE DRAWINGS

FIGS. 1–4 show by way of example possible embodiments of devices designed according to the invention, wherein:

DETAILED DESCRIPTION OF THE INVENTION

Figure 1:
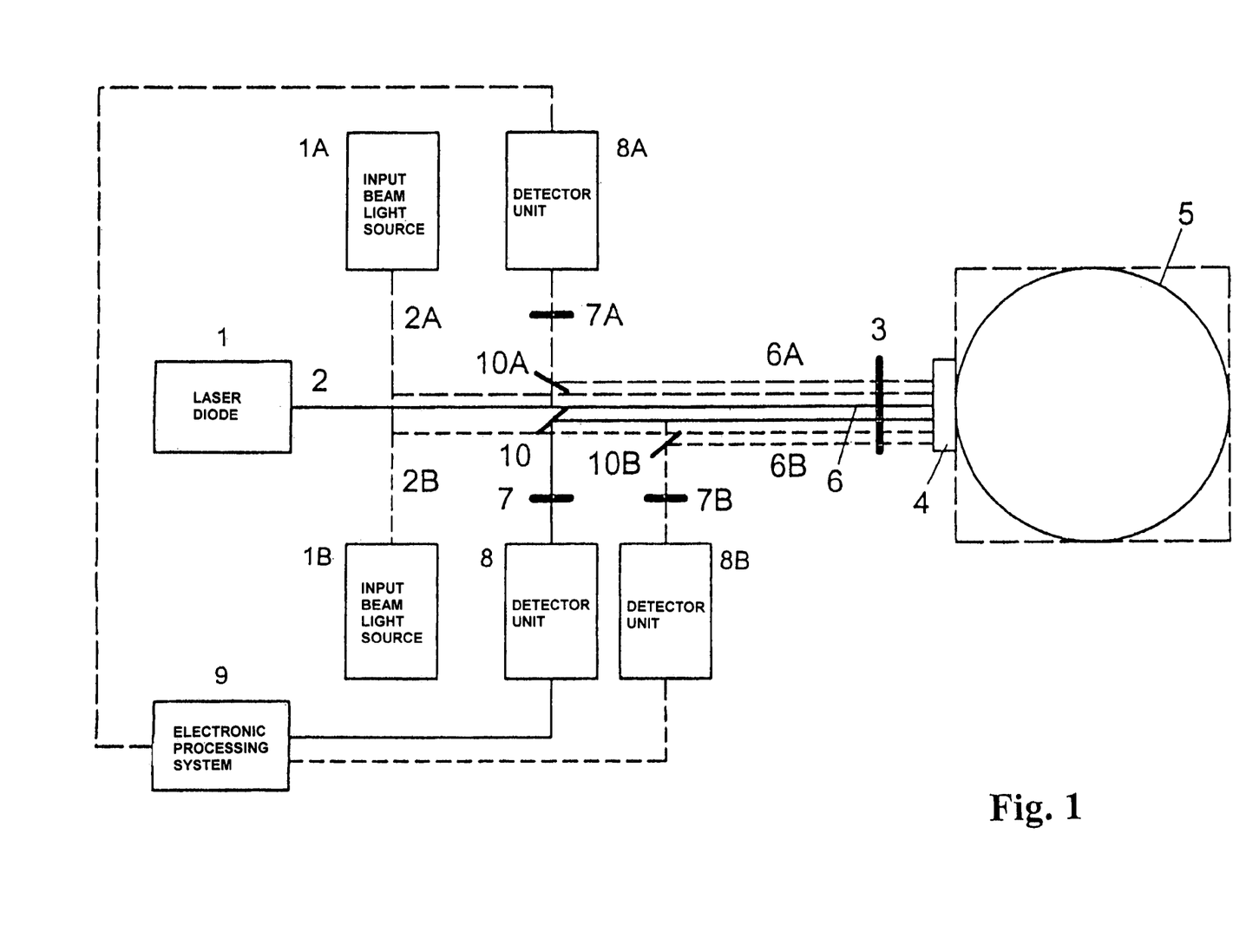
FIG. 1 shows a device in which a detection side is constructed on the same side of the test area on which the input beam side is also located (backscatter arrangement)
Figure 2:
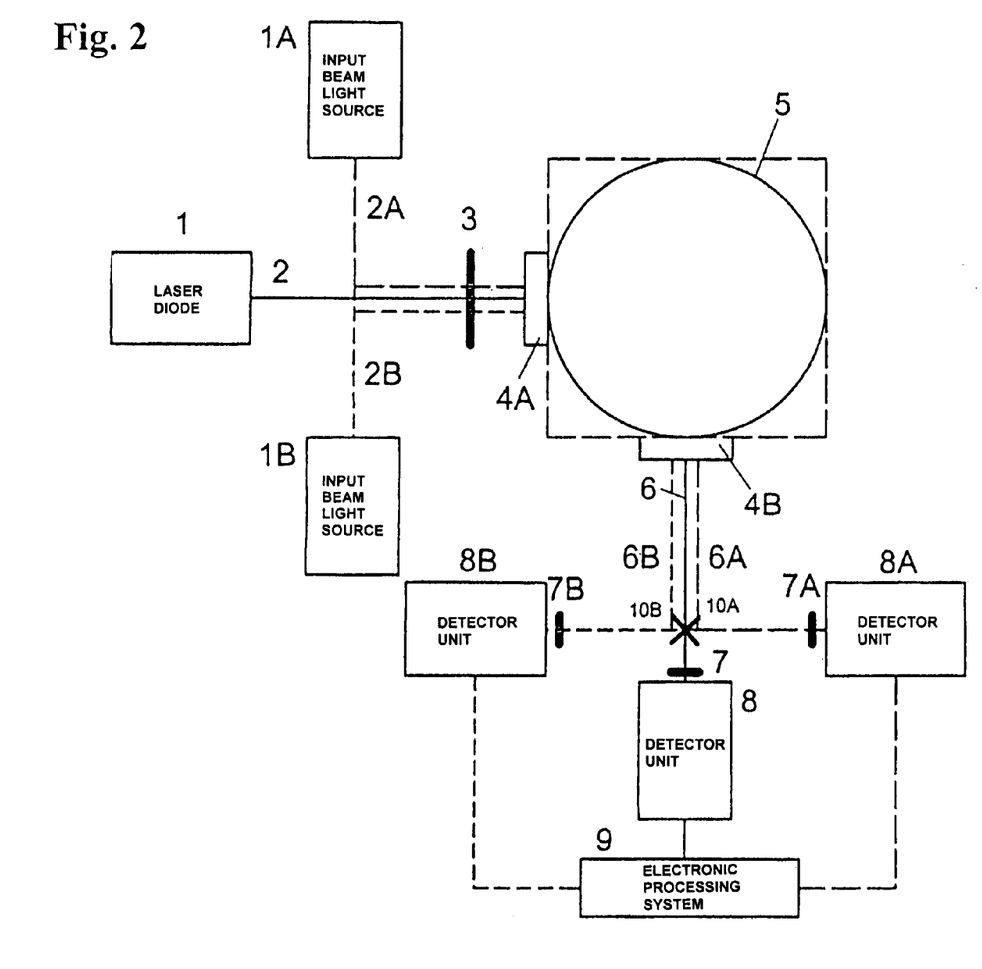
FIG. 2 shows a device according to the invention in which by way of example input beam and recording beam form a 90 degree arrangement for three different techniques.
Figure 3:
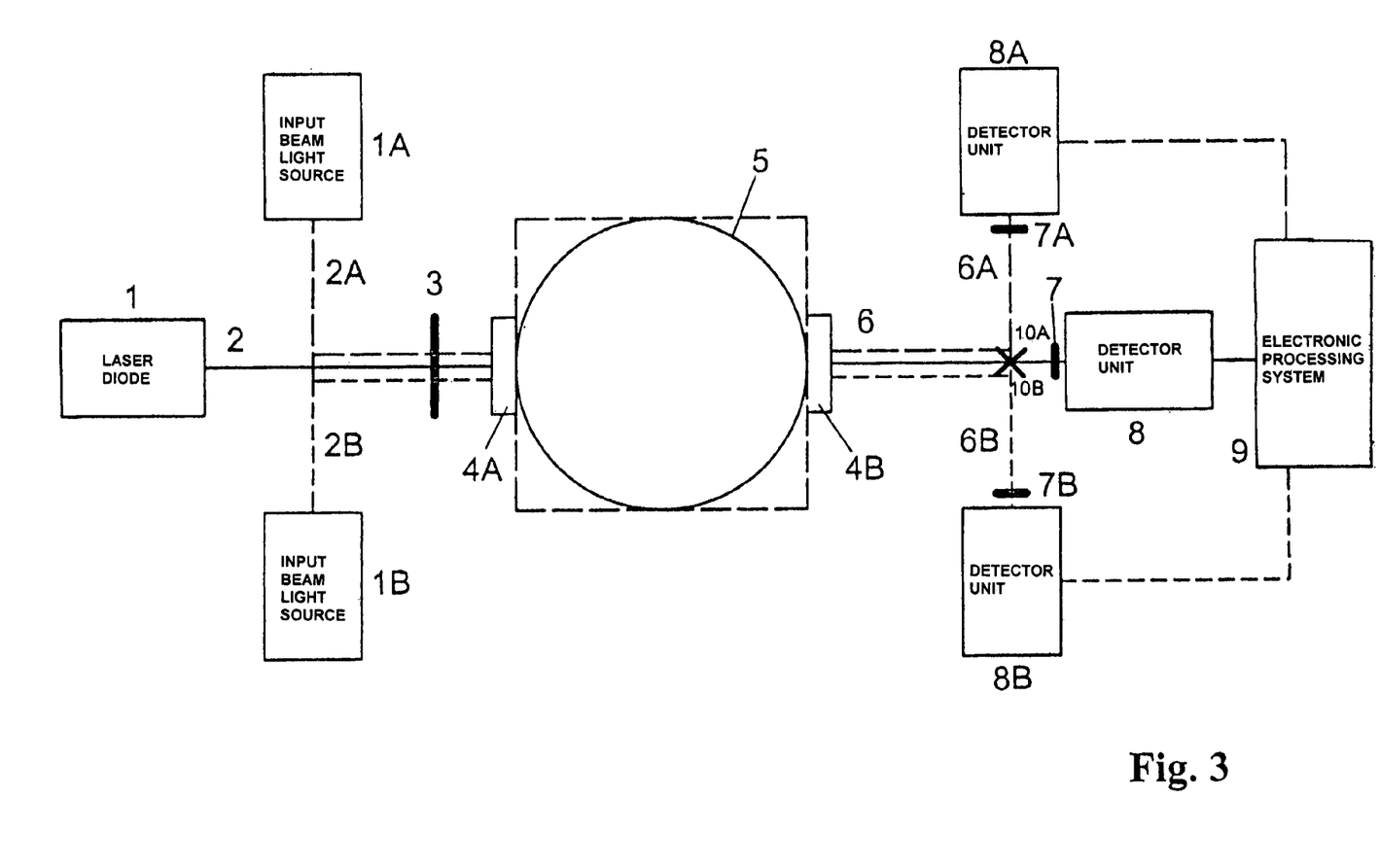
FIG. 3 shows a device according to the invention in diagrammatic form in which the signal beam course is constructed behind the test volume, thus opposite the input beam side (thus as a 180-degree or transmission arrangement)

Possible embodiments of devices designed according to the invention are shown by way of example in FIGS. 1 through 3, in which only those devices are represented in which several of the above-mentioned processes are used in combination simultaneously or one after the other. Advantageously, in the devices optical components of the input beam course and detection beam course provided with measures for avoiding or minimizing contamination (e.g., air-rinsed, heated, etc.) are included in a device comprising the test volume (e.g., ring or channel segment), e.g., according to patent application DE 19904691 A1, through which the raw exhaust gas and/or pretreated or aftertreated exhaust gas can flow without special dilution and unconditioned (e.g., cooled or heated) and can thereby be characterized according to the invention. Alternatively, devices can also be constructed in which according to the invention only the linear Raman scattering (LRS) is used to characterize the liquid and/or solid particles and/or gaseous constituents of the exhaust gas and/or only laser-induced breakdown spectroscopy. (LIBS) is used for the solid particles and/or only the laser (diode) absorption technique (LAT) using variable radiation sources is used to record the gaseous exhaust gas constituents, alone or in combination with one another or in particular with the LII technique for recording the soot particle values.

FIG. 1 shows a device of this type in which the detection side is constructed on the same side of the test area on which the input beam side is also located (backscatter arrangement). Such an arrangement has the advantage that it requires only one optical access to the test area. A laser, a diode laser or a laser diode that radiates its excitation light beam into the test volume via an optical beam course 2 through an optical access 4, which is advantageously provided with a device (e.g., heating or air rinsing) for avoiding or reducing contamination, serves as the excitation light source 1, which test volume is located inside a pipe or channel segment 5 that can be directly installed in the exhaust gas pipe and thus can directly measure the raw exhaust gas or the treated exhaust gas without conditioning. An optical device 3 in front of the segment access, e.g., a lens or a combination of several lenses, one or more apertures, etc., can have a favorable influence on the beam course for the test area, e.g., by expanding or focusing it. The beam course 2 can also be favorably composed with the use of optical fibers, completely between the laser 1 and the optical access 4 or also only in partial areas thereof.

With the backscattering arrangement in FIG. 1, the recording beam course 6, which can likewise be partially or completely composed of optical fibers, leaves the test area 5 on the same side e.g., inside the circle or pipe segment, on which the input beam also takes place. This can take place via the same optical access or via one of this type in the immediate vicinity. The measurement signal is also conveyed to a detector unit 8 in the beam course 6 parallel to the input beam, if necessary even using the same beam course 2, or also independent of it. When using the same beam course 2 and 6 another optical element 10 is placed in the beam course, which element spatially divides the signal beam course from the input beam and deflects it in the direction of the detector unit 8. An optical unit 7 is located in front of the detector 8, which unit differs according to the process, and which, e.g., can be composed of apertures, lenses and in particular also different filters (gray filters, interference filters and/or cut-off filters) or also in combination with spectrographs or monochromators, with the aid of which the measuring signal is processed according to the desired signal information in terms of intensity and/or spectrally. The detector unit 8, e.g., one or more photomultipliers, one or more photodiodes, one or more CCD or streak cameras, or also combinations of several such optoelectronic components, processes the optical signal into an electric datum that can be further processed in an electronic processing system 9, e.g., a computer, a correlator, etc., and processed for use, e.g., in measuring circuits and closed loops in, e.g., test bed peripheral equipment, as a control system also, e.g., in combination with on-board diagnostics (OBD) in the vehicle itself.

FIG. 1 shows by way of example three different measuring processes according to the device connected in an arrangement, whereby according to the invention the above-mentioned LIBS, LAF and LRS techniques can be combined with the LII technique or also LAT instead of LIBS, LAF or LRS, provided that the output of a multi-pass device used is located on the input beam side (in general at least one irradiation direction according to FIG. 3 is required for LAT). With a suitable choice of the input beam light source 1, all measuring processes can be operated from only one light source or alternatively also with different input beam light sources (1A and 1B additionally) specially optimized for the respective process. The same applies to the input beam courses 2, 2A, 2B and recording beam courses 6, 6A, 6B, the detector units 8, 8A, 8B used and the optical elements 7, 7A, 7B placed in front thereof. If all three processes are provided with specific beam courses and the same beam courses can be used for input beam and signal detection, separating and if necessary also deflecting optical elements 10, 10A, 10B should be included in each one of them. Such elements are also used to separate different signal beams if they use the same beam course from the test object.

Alternatively to FIG. 1, FIG. 2 shows a device according to the invention in which by way of example input beam and recording beam here again form a 90 degree arrangement for three different techniques. The description of FIG. 1, with all statements and conclusions, is also applicable to FIG. 2 in its entirety, except that here for device-related reasons elements 10A and 10B no longer separate input beam and signal beam from one another, but here only different signal beam courses according to the different measuring processes.

The same applies to FIG. 3, where a device according to the invention is shown in diagrammatic form, in which the signal beam course is constructed behind the test volume, thus opposite the input beam side (thus as a 180-degree or transmission arrangement). Such an arrangement provides the simplest method for combinative inclusion of the LAT process.

In addition to the devices shown in diagrammatic form in FIGS. 1–3, according to the invention all possible combination forms can also be embodied separately regarding the position of input beam and recording beam course relative to the test area and relative to one another for all referenced measuring processes, whereby angled arrangements, other than 0, 90 and 180 degrees, can be selected for individual and/or all referenced measuring processes.

Figure 4:
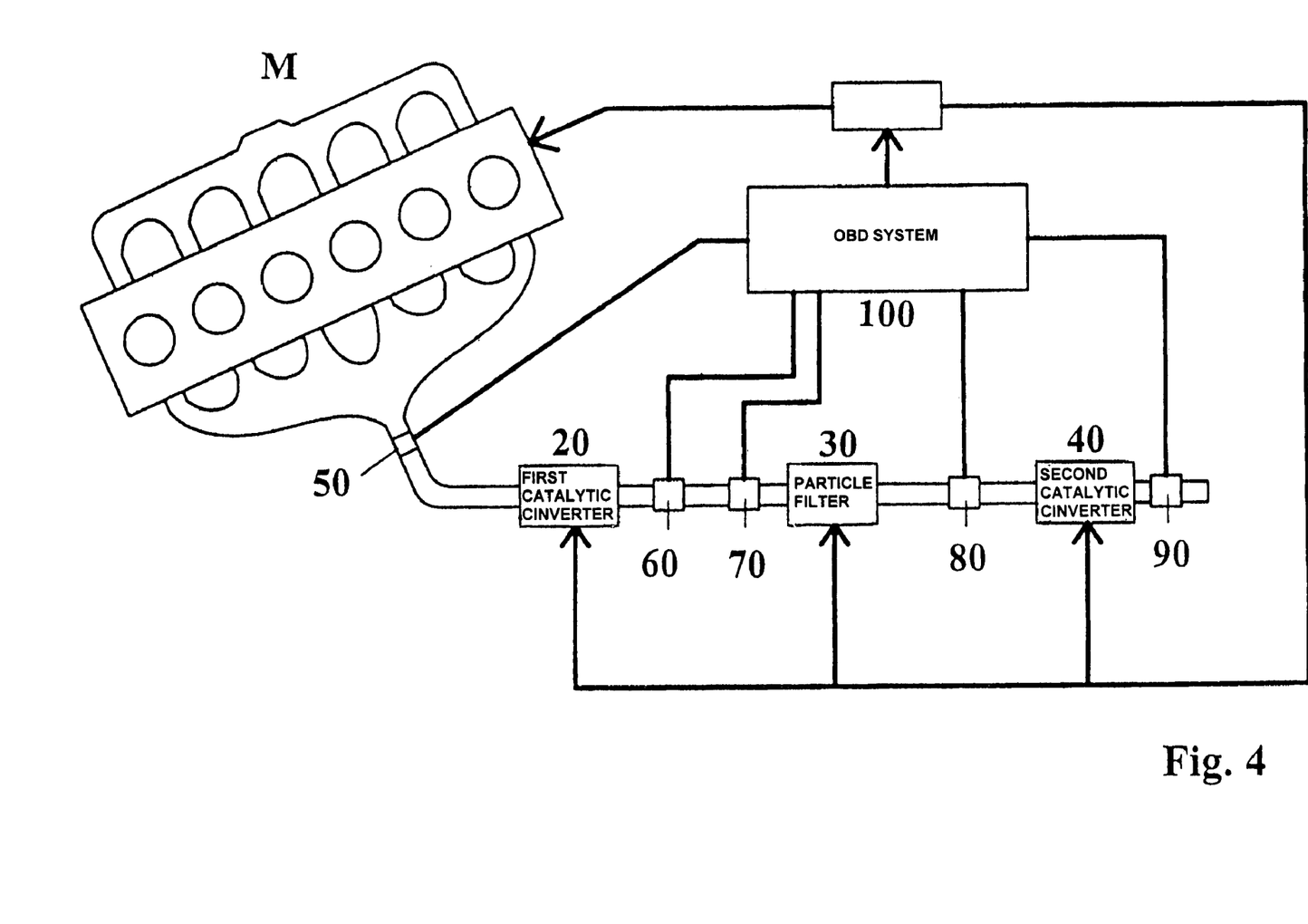
FIG. 4 shows in diagrammatic form a possible application of the invention in the testing and characterization of an engine exhaust gas.

FIG. 4 shows in diagrammatic form a possible application of the invention in the testing and characterization of an engine exhaust gas in raw state behind the exhaust gas manifold of an engine M and in front of, e.g., a first catalytic converter 20, e.g., an oxidation catalytic converter, at the measuring point 50, of the treated exhaust gas behind the catalytic converter 20 at the measuring point 60 and at the measuring point 70 in front of, e.g., a particle filter 30—measuring points 60 and 70 could also represent only one measuring point according to the invention—and behind this at measuring point 80 which again can be placed simultaneously or separately in several measuring points, e.g., in front of a second catalytic converter 40, e.g., a $NO_x$ storage catalytic converter. Another measuring point 90, for example, is then located behind this catalytic converter 40, from which measuring point—as from all the other measuring points as well—the measured information is passed to the test bed peripheral equipment or the central unit of an OBD system 100 which then, e.g., in the latter case also can have an active influence on the engine operation or the individual components of the exhaust gas aftertreatment. These principles are also applicable to any other exhaust gas system, regardless of its respective composition and differently for spark ignition engine and diesel engine applications. In this case, a device with LII, LIBS, LRS and LAT (in particular ë) could be installed e.g. at measuring point 50, that with LAT and/or LRS and LII or also LIBS at the measuring points 60 and 70, possibly alternatively to 50, LAT (in particular ë), LII and LIBS (and/or LRS) at measuring point 80 and LAT (i.a., also in particular NH3) and LRS at measuring point 90. Many other groupings and combinations are useful and provided according to the invention. Some of the measuring points are equipped in connection with a sensor to record the exhaust gas temperature, which is already contained in the LII sensor according to the invention (German patent application DE 19904691 A1).

The invention claimed is:

1. A process for determining properties of liquid particles of engine exhaust gas, the process comprising:
   detecting Raman scattering produced in a test area by excitation with one of a laser, a laser diode, and a diode laser; and
   determining at least one of:
      a type and composition of individual constituents of the liquid particles of the engine exhaust gas, and
      concentrations of individual constituents of the liquid particles of the engine exhaust gas.

2. The process of claim 1, wherein the determining comprises determining concentrations of the individual constituents of the liquid particles of the engine exhaust gas, and wherein the concentrations of individual constituents of the liquid particles of the engine exhaust gas comprise at least one of a number concentration, a mass concentration, and a volume concentration.

3. The process of claim 1, wherein the determining comprises determining concentrations, via partial densities, of the individual constituents of the liquid particles of the engine exhaust gas, and wherein the concentrations of individual constituents of the liquid particles of the engine exhaust gas comprise at least one of a number concentration, a mass concentration, and a volume concentration.

4. The process of claim 1, wherein the engine exhaust gas is in a raw state.

5. The process of claim 1, wherein the engine exhaust gas is at least one of conditioned exhaust gas and diluted exhaust gas.

6. The process of claim 1, wherein the engine exhaust gas comprises one of water, sulfuric acid, nitric acid, water in pure form, sulfuric acid in pure form, nitric acid in pure form.

7. The process of claim 1, wherein the engine exhaust gas comprises at least one of other constituents and aqueous solutions.

8. The process of claim 1, wherein the engine exhaust gas comprises an urea water solution.

9. The process of claim 1, wherein the engine exhaust gas comprises a mixture of one of water, sulfuric acid, nitric acid, and water in pure form, sulfuric acid in pure form, nitric acid in pure form.

10. The process of claim 1, wherein the process determines properties of liquid particles of engine exhaust gas behind components of exhaust gas aftertreatment.

11. A process for determining properties of solid particles of engine exhaust gas, the process comprising:
    detecting Raman scattering produced in a test area by excitation with one of a laser, a laser diode, and a diode laser; and
    determining at least one of:
       a type and composition of individual constituents of the solid particles of the engine exhaust gas, and
       concentrations of individual constituents of the solid particles of the engine exhaust gas.

12. The process of claim 11, wherein the determining comprises determining concentrations of individual constituents of the solid particles of the engine exhaust gas, and wherein the concentrations of individual constituents of the solid particles of the engine exhaust gas comprise at least one of a number concentration, a mass concentration, and a volume concentration.

13. The process of claim 11, wherein the determining comprises determining concentrations of individual constituents of the solid particles of the engine exhaust gas, and wherein the concentrations of individual constituents of the solid particles of the engine exhaust gas comprise at least one of a number concentration, a mass concentration, and a volume concentration.

14. The process of claim 11, wherein the engine exhaust gas is in a raw state.

15. The process of claim 11, wherein the engine exhaust gas is at least one of conditioned exhaust gas and diluted exhaust gas.

16. The process of claim 11, wherein the solid particles comprise one of soot particles, metals, metal oxides, metal compounds, silicon compounds, and ash.

17. The process of claim 11, wherein the process determines properties of solid particles of engine exhaust gas behind components of exhaust gas aftertreatment.

18. A process for determining properties of solid particles of engine exhaust gas, the process comprising:
    detecting radiation produced in a test area by laser-induced breakdown spectroscopy (LIBS) after irradiation with one of a laser, a laser diode, and a diode laser; and
    determining a type and composition of the solid particles of the engine exhaust gas.

19. The process of claim 18, wherein the engine exhaust gas is in a raw state.

20. The process of claim 18, wherein the engine exhaust gas is at least one of conditioned exhaust gas and diluted exhaust gas.

21. The process of claim 18, wherein the solid particles comprise one of soot particles, metals, metal oxides, metal compounds, silicon compounds, and ash.

22. The process of claim 18, wherein the process determines properties of solid particles of engine exhaust gas behind components of exhaust gas aftertreatment.

23. A process for determining properties of solid particles of engine exhaust gas, the process comprising:
    detecting radiation produced in a test area after irradiation with one of a laser, a laser diode, and a diode laser, and after vaporization and ionization of one of the solid particles and parts of the solid particles; and
    determining a type and composition of the solid particles of the engine exhaust gas.

24. The process of claim 23, wherein the engine exhaust gas is in a raw state.

25. The process of claim 23, wherein the engine exhaust gas is at least one of conditioned exhaust gas and diluted exhaust gas.

26. The process of claim 23, wherein the solid particles comprise one of soot particles, metals, metal oxides, metal compounds, silicon compounds, and ash.

27. The process of claim 23, wherein the process determines properties of solid particles of engine exhaust gas behind components of exhaust gas aftertreatment.

28. A process for determining properties of liquid particles of engine exhaust gas, the process comprising:
    detecting radiation produced in a test area after irradiation with one of a laser, a laser diode, and a diode laser, and after vaporization and ionization of one of the liquid particles and parts of the liquid particles; and
    determining a type and composition of the liquid particles of the engine exhaust gas.

29. The process of claim 28, wherein the engine exhaust gas is in a raw state.

30. The process of claim 28, wherein the engine exhaust gas is at least one of conditioned exhaust gas and diluted exhaust gas.

31. The process of claim 28, wherein the engine exhaust gas comprises one of water, sulfuric acid, nitric acid, water in pure form, sulfuric acid in pure form, nitric acid in pure form.

32. The process of claim 28, wherein the engine exhaust gas comprises at least one of other constituents and aqueous solutions.

33. The process of claim 28, wherein the engine exhaust gas comprises an urea water solution.

34. The process of claim 28, wherein the engine exhaust gas comprises a mixture of one of water, sulfuric acid, nitric acid, and water in pure form, sulfuric acid in pure form, nitric acid in pure form.

35. The process of claim 28, wherein the process determines properties of liquid particles of engine exhaust gas behind components of exhaust gas aftertreatment.

36. A process for determining properties of liquid particles of engine exhaust gas, the process comprising:
    detecting radiation produced in a test area by laser-induced breakdown spectroscopy (LIBS) after irradiation with one of a laser, a laser diode, and a diode laser; and
    determining a type and composition of the liquid particles of the engine exhaust gas.

37. The process of claim 36, wherein the engine exhaust gas is in a raw state.

38. The process of claim 36, wherein the engine exhaust gas is at least one of conditioned exhaust gas and diluted exhaust gas.

39. The process of claim 36, wherein the engine exhaust gas comprises one of water, sulfuric acid, nitric acid, water in pure form, sulfuric acid in pure form, nitric acid in pure form.

40. The process of claim 36, wherein the engine exhaust gas comprises at least one of other constituents and aqueous solutions.

41. The process of claim 36, wherein the engine exhaust gas comprises an urea water solution.

42. The process of claim 36, wherein the engine exhaust gas comprises a mixture of one of water, sulfuric acid, nitric acid, and water in pure form, sulfuric acid in pure form, nitric acid in pure form.

43. The process of claim 36, wherein the process determines properties of liquid particles of engine exhaust gas behind components of exhaust gas aftertreatment.

44. A process for determining concentrations of gaseous constituents of engine exhaust gas, the process comprising:
    detecting radiation produced in a test area by laser-induced breakdown spectroscopy (LIBS) after irradiation with one of a laser, a laser diode, and a diode laser; and
    determining a type and concentration of individual gaseous constituents of the engine exhaust gas.

45. The process of claim 44, wherein the concentration of individual gaseous constituents of engine exhaust gas comprises one of:
    a number concentration of individual gaseous constituents of engine exhaust gas;
    a mass concentration of individual gaseous constituents of engine exhaust gas; and
    a volume concentration of individual gaseous constituents of engine exhaust gas.

46. The process of claim 44, wherein the engine exhaust gas is in a raw state.

47. The process of claim 44, wherein the engine exhaust gas is at least one of conditioned exhaust gas and diluted exhaust gas.

48. The process of claim 44, wherein the individual gaseous constituents comprise $NO_x$, NO, $NO_2$, $N_2O$, CO, HC, $O_2$, $H_2O$, and $NH_3$.

49. The process of claim 44, wherein the process determines concentrations of gaseous constituents of engine exhaust gas behind components of exhaust gas aftertreatment.

50. A process for determining properties of at least one of liquid particles and solid particles of engine exhaust gas, the process comprising:
    detecting an atomic fluorescence emission produced in a test area by excitation with one of a laser, a laser diode, and a diode laser; and
    determining a type and composition of the liquid and/or solid particles of the engine exhaust gas and concentrations of individual constituents.

51. The process of claim 50, wherein the engine exhaust gas is in a raw state.

52. The process of claim 50, wherein the engine exhaust gas is at least one of conditioned exhaust gas and diluted exhaust gas.

53. The process of claim 50, further comprising determining concentrations of individual constituents, which concentrations comprise at least one of a number concentration, a mass concentration and a volume concentration.

54. The process of claim 50, further comprising calculating concentrations of individual constituents using at least one of a measuring signal and an atomic fluorescence measuring signal.

55. The process of claim 50, further comprising, after ionization, calculating concentrations of individual constituents using at least one of a measuring signal and an atomic fluorescence measuring signal.

56. The process of claim 50, wherein the engine exhaust gas comprises one of water, sulfuric acid, nitric acid, water in pure form, sulfuric acid in pure form, nitric acid in pure form.

57. The process of claim 50, wherein the engine exhaust gas comprises at least one of other constituents and aqueous solutions.

58. The process of claim 50, wherein the engine exhaust gas comprises an urea water solution.

59. The process of claim 50, wherein the engine exhaust gas comprises a mixture of one of water, sulfuric acid, nitric acid, and water in pure form, sulfuric acid in pure form, nitric acid in pure form.

60. The process of claim 50, wherein the solid particles comprise one of soot particles, metals, metal oxides, metal compounds, silicon compounds, and ash.

61. The process of claim 50, wherein the process determines properties of at least one of liquid particles and solid particles of engine exhaust gas behind components of exhaust gas aftertreatment.

62. A process for determining properties of solid particles of engine exhaust gas, the process comprising:
    detecting radiation produced in a test area by laser-induced breakdown spectroscopy (LIBS) after irradiation with one of a laser, a laser diode, and a diode laser;
    detecting radiation produced in the test area by laser-induced incandescence (LII) after irradiation with one of a laser, a laser diode, and a diode laser; and determining a type and composition of the solid particles of the engine exhaust gas.

63. A process for determining properties of liquid particles of engine exhaust gas, the process comprising:
  detecting radiation produced in a test area by laser-induced breakdown spectroscopy (LIBS) after irradiation with one of a laser, a laser diode, and a diode laser;
  detecting radiation produced in the test area by laser-induced incandescence (LII) after irradiation with one of a laser, a laser diode, and a diode laser; and
  determining a type and composition of the liquid particles of the engine exhaust gas.

64. A process for determining concentrations of gaseous constituents of engine exhaust gas, the process comprising:
  detecting radiation produced in a test area by laser-induced breakdown spectroscopy (LIBS) after irradiation with one of a laser, a laser diode, and a diode laser;
  detecting radiation produced in the test area by laser-induced incandescence (LII) after irradiation with one of a laser, a laser diode, and a diode laser; and
  determining a type and concentration of individual gaseous constituents of the engine exhaust gas.

65. A process for determining properties of liquid particles of engine exhaust gas, the process comprising:
  detecting Raman scattering produced in a test area by excitation with one of a laser, a laser diode, and a diode laser;
  detecting radiation produced in the test area by laser-induced incandescence (LII) after irradiation with one of a laser, a laser diode, and a diode laser; and
  determining at least one of:
    a type and composition of individual constituents of the liquid particles of the engine exhaust gas, and
    concentrations of individual constituents of the liquid particles of the engine exhaust gas.

66. A process for determining properties of solid particles of engine exhaust gas, the process comprising:
  detecting Raman scattering produced in a test area by excitation with one of a laser, a laser diode, and a diode laser;
  detecting radiation produced in the test area by laser-induced incandescence (LII) after irradiation with one of a laser, a laser diode, and a diode laser; and
  determining at least one of:
    a type and composition of individual constituents of the solid particles of the engine exhaust gas, and
    concentrations of individual constituents of the solid particles of the engine exhaust gas.

\* \* \* \* \*